US011730554B2

(12) United States Patent
Thompson et al.

(10) Patent No.: US 11,730,554 B2
(45) Date of Patent: Aug. 22, 2023

(54) REMOVABLE DEVICE COVERS

(71) Applicant: Precision Dynamics Corporation, Valencia, CA (US)

(72) Inventors: Jennifer Thompson, Santa Clarita, CA (US); Jessie Rios, Santa Clarita, CA (US)

(73) Assignee: Precision Dynamics Corporation, Valencia, CA (US)

( * ) Notice: Subject to any disclaimer, the term of this patent is extended or adjusted under 35 U.S.C. 154(b) by 1477 days.

(21) Appl. No.: 15/963,976

(22) Filed: Apr. 26, 2018

(65) Prior Publication Data

US 2019/0328476 A1    Oct. 31, 2019

(51) Int. Cl.
*A61B 46/10*   (2016.01)
*A61B 46/00*   (2016.01)
*A61B 6/00*    (2006.01)
*A61B 46/23*   (2016.01)
*A61B 46/20*   (2016.01)

(52) U.S. Cl.
CPC ............ *A61B 46/10* (2016.02); *A61B 6/4423* (2013.01); *A61B 46/40* (2016.02); *A61B 46/23* (2016.02); *A61B 2046/205* (2016.02)

(58) Field of Classification Search
CPC ... A61B 46/10; A61B 46/40; A61B 2046/205; A61B 46/00; A61B 46/13; A61B 46/17; A61B 46/20; A61B 2046/234; A61B 2046/236; A61B 2046/201; A61B 46/23
See application file for complete search history.

(56) References Cited

U.S. PATENT DOCUMENTS

| | | | |
|---|---|---|---|
| 6,105,578 A * | 8/2000 | Sommers | A61B 46/10 128/853 |
| 6,458,110 B1 * | 10/2002 | Lavon | A61F 13/495 604/385.12 |
| D854,186 S * | 7/2019 | Thompson | D24/231 |
| 2003/0181810 A1 * | 9/2003 | Murphy | A61L 31/18 600/427 |
| 2006/0135932 A1 * | 6/2006 | Abuto | A61F 13/531 604/368 |

(Continued)

FOREIGN PATENT DOCUMENTS

| | | | |
|---|---|---|---|
| WO | WO 2007/027221 A1 * | 3/2007 | |
| WO | WO 2011/032206 A1 * | 3/2011 | |

*Primary Examiner* — Camtu T Nguyen
(74) *Attorney, Agent, or Firm* — Quarles & Brady LLP

(57) ABSTRACT

The present disclosure provides example device covers implementing differential adhesive systems allowing for clean removal of the cover after a prolonged dwell period. An example device cover comprises a bore section, a first drape section extending from a first end of the bore section, and a second drape section extending from a second end of the bore section. A first edge of the first drape section may extend from the first end of the bore section at approximately a 50° angle, a second edge of the first drape section may extend from the first end of the bore section at approximately a 130° angle. The first drape section and second drape section may be symmetrical with respect to each other. The device cover may further comprise one or more adhesive tabs, each comprising an intermediary body with a first acrylic adhesive layer and an opposite second rubber adhesive layer.

20 Claims, 11 Drawing Sheets

(56) References Cited

U.S. PATENT DOCUMENTS

| | | | |
|---|---|---|---|
| 2007/0023053 A1* | 2/2007 | Bowen | A61B 46/30 128/853 |
| 2007/0049891 A1* | 3/2007 | Clark | A61F 13/5513 604/385.13 |
| 2009/0141853 A1* | 6/2009 | Crews | A61B 6/032 378/4 |
| 2012/0237000 A1* | 9/2012 | Rahme | A61B 6/10 378/204 |
| 2015/0114404 A1* | 4/2015 | Czop | A61B 46/10 128/856 |
| 2017/0265957 A1* | 3/2017 | Clapper | C09J 5/00 |
| 2017/0066863 A1* | 9/2017 | Chua | A61B 50/30 |
| 2022/0022829 A1* | 1/2022 | Oakes | A61B 46/40 |

\* cited by examiner

Top view

REMOVABLE DEVICE COVERS

TECHNICAL FIELD

The present disclosure generally relates to covers and more specifically to removable device covers.

BACKGROUND

A plastic article is often applied over devices to serve as a protective barrier for prolonged, but temporary periods of time. Such plastic articles are often large plastic coverings used to protect items during a temporary process. For example, to protect equipment during a procedure, or components during product manufacture or maintenance.

A cover is often applied between a patient and a device to serve as a protective barrier to fluids for the device or to create a sterile barrier. Existing covers are difficult to place by a single gloved professional, difficult to fit and problematic to remove. Existing covers also leave adhesive residues on a device, especially in practice where operational realities mean that covers are allowed to dwell on a device for hours or days between uses. Over time, such residues will collect dust and dirt which is not desired in a setting, and which typically require the use of solvents that may be harmful and toxic to humans and require proper storage safety.

Effective adhesive solutions for plastic protective barriers should, therefore, not only support a plastic barrier on a surface for a prolonged but temporary period of time, the adhesive solution should also be cleanly removable without tearing the plastic barrier or leaving residue on the surface. The above identified technical problems are reduced or eliminated by the systems and methods disclosed in the present disclosure.

SUMMARY

Embodiments of removable device covers, as well as method and computer executable instructions for manufacturing the same are provided in the present disclosure.

In one aspect, which may include at least a portion of the subject matter of any of the preceding and/or following examples and aspects, example device covers are described which implement differential adhesive systems allowing for clean removal of the cover after a prolonged dwell period. The device cover comprises a bore section, a first drape section extending from a first end of the bore section, and a second drape section extending from a second end of the bore section. A first edge of the first drape section may extend from the first end of the bore section at approximately a 50° angle, a second edge of the first drape section may extend from the first end of the bore section at approximately a 130° angle. The first drape section and second drape section may be symmetrical with respect to each other.

The device cover further comprises one or more adhesive tabs. Each adhesive tab comprises an intermediary body having a first side and an opposite second side, a first adhesive layer attached to the first side, and a second adhesive layer attached to the second side. The first adhesive layer comprises an acrylic adhesive, and the second adhesive layer comprises a rubber adhesive secured to the device cover.

The first adhesive layer of each adhesive tab may be covered by a liner layer. The dimension of each side of the liner layer is greater than the dimension of each side of the corresponding differential adhesive. The device cover may further comprise one or more instruction labels including instructions for operating the device cover. The instruction labels may be of a different visual indication (e.g., color) than the liner layers. The one or more adhesive tabs are located on one or more of the following: the bore section, the first drape section, and the second drape section.

A first set of the one or more adhesive tabs are configured for releasably attaching the device cover to a surface of a first object, and wherein a second set of the one or more adhesive tabs are configured for releasably attaching the device cover to a surface of a second object.

In some embodiments, the intermediary body comprises a polyester film. The acrylic adhesive of the first adhesive layer may include a peel adhesion of approximately 40 ounces per inch to approximately 60 ounces per inch. The acrylic adhesive of the first adhesive layer may comprise a cross-linked pressure sensitive acrylic adhesive.

The first adhesive layer may be configured for releasable attachment to the surface of a first object. The first object may be a CT scanner. The second adhesive layer may be configured for permanent attachment to the device cover.

The device cover may comprise a covering of plastic material. In some embodiments, the device cover comprises a polyethylene film. The bore section may be configured to fit within the bore of a computed tomography (CT) scanner. In some embodiments, the plastic article is radiolucent. In some embodiments, the device cover is sterilizable.

Other implementations of this disclosure include corresponding devices, systems, and computer programs, as well as and associated methods for operating and manufacturing the described devices and systems. These other implementations may each optionally include one or more of the following features. For instance, provided is a method of attaching a device cover to a surface of a device. The method comprises placing a bore section of the device cover at the center of a bore of the device. The method further comprises unfolding a first drape section extending from a first end of the bore section. A first edge of the first drape section extends from the first end of the bore section at approximately a 50° angle, and a second edge of the first drape section extends from the first end of the bore section at approximately a 130° angle. The method further comprises unfolding a second drape section extending from a second end of the bore section. The first drape section and second drape section are symmetrical with respect to each other.

The method may further comprise removing a liner layer from an adhesive tab secured to the device cover, and applying the exposed adhesive tab to the surface of the device. As described, the adhesive tab may comprise an intermediary body having a first side and an opposite second side, a first adhesive layer attached to the first side, and a second adhesive layer attached to the second side. The first adhesive layer may comprise an acrylic adhesive covered by the liner, and the second adhesive layer may comprise a rubber adhesive secured to the device cover.

These and other embodiments are described further below with reference to the figures.

BRIEF DESCRIPTION OF THE DRAWINGS

Embodiments of the present disclosure and their advantages are best understood by referring to the detailed description that follows. Like reference numbers identify like elements illustrated in one or more of the figures.

DETAILED DESCRIPTION

Figure 1A:
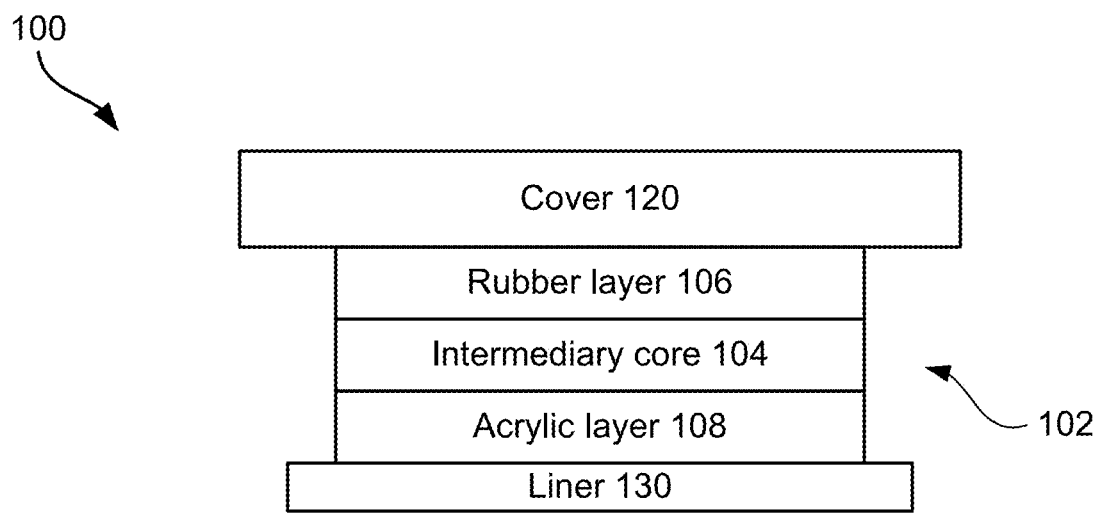
FIGS. 1A and 1B illustrate an enlarged fragmentary vertical section of a differential adhesive system in accordance with various embodiments of the present disclosure.

The present disclosure provides example adhesives and device covers that can be implemented with various embodiments of the present disclosure.

Overview

Often devices require protective covers to create a protective barrier to fluids for the device, or to create a sterile barrier between a patient and the device. Such covers may maintain sterile or hygienic standard in a clinical setting, as well as protect the equipment from bodily fluids and spills and leakages. Such devices may include imaging equipment used by hospitals and imaging centers, such as Computed Tomography (CT) machines or Magnetic Resonance Imaging (MRI) machines. Such devices may include surfaces comprising painted metal or plastic, and which may be textured.

Existing covers implement either a rubber adhesive or an acrylic adhesive. Such existing covers are difficult to place by one person, difficult to fit well and problematic to remove. For example, existing covers have to be removed shortly after use to be cleanly removed. Otherwise, adhesive residues may remain on the device after removal. Over time, any residual adhesive will collect dust and dirt which is not desired in a clinical setting. Residual adhesive removal typically requires the use of solvents that are harmful and toxic and require proper storage safety.

Typically device covers are fabricated from plastic, such as polyethylene film, which includes a low surface energy. Most pressure sensitive adhesives (PSAs) cannot functionally hold such plastic covers onto the surface of a device. Acrylic PSAs preferentially adhere to the device instead of the polyethylene cover due to low bond strength with polyethylene film. Rubber PSAs generally include stronger bond strengths to polyethylene film, as well high bond strength to device surfaces. As a result, rubber PSAs require a high peel force to remove which can cause the polyethylene cover to tear, or which can leave residual adhesive on the device surface during removal.

The technologies described in the present disclosure can provide the following technical advantages. First, the described differential adhesive systems are capable of adhering to a first side or surface of a cover with a low surface energy and supporting the cover upon another surface, such as that of a device. Second, the described adhesion systems are capable of supporting a cover on the surface for prolonged periods of time, such as overnight or over a weekend. Furthermore, the adhesion system allows the cover and adhesives to be cleanly removed after such prolonged periods (i.e., a 24 hour dwell) without leaving residue on the surface.

The technologies described in the present disclosure therefore provides a secure attachment without leaving behind residue on the machine that will collect dust and dirt, which is not desired, especially in a setting. Additionally, these technologies eliminate or reduce the need for and exposure to chemicals and solvents for removing adhesive residue, which require special storage requirements and additional labor. Additional details of implementations are now described in relation to the Figures.

Example Embodiments

Figure 1B:
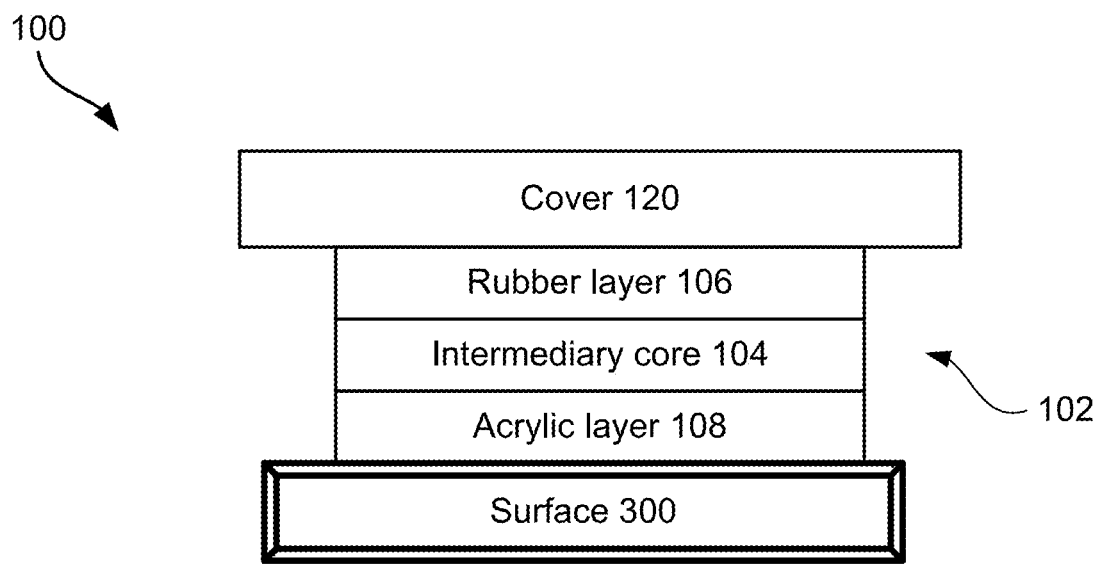

The present disclosure describes a differential adhesive system comprising a removable acrylic adhesive layer and a permanent rubber adhesive layer. FIGS. 1A and 1B illustrate an enlarged fragmentary vertical section of a differential adhesive system 100, in accordance with one or more embodiments. As illustrated in FIGS. 1A and 1B, a differential adhesive system 100 includes differential adhesive 102 comprising intermediary core 104, rubber layer 106 and acrylic layer 108. In various embodiments, differential adhesive system further includes cover 120.

In various embodiments, intermediary core 104 comprises a polyester film. In other embodiments, intermediary core 104 may comprise a polyethylene film. As used herein, intermediary core may be referred to herein as a "carrier" or "carrier film" or "intermediary film" or "intermediary body" or "intermediary core layer." Rubber layer 106 and acrylic layer 108 are located on opposite sides of the intermediary core layer 104. This construction may be manufactured by coating one side of the intermediary core layer 104 with adhesive, laminating in a liner, then coating the opposite side of the intermediary core layer 104. Alternatively, one of the adhesives could be coated onto a release liner and that adhesive subsequently laminated to the opposite side of the previously adhesive coated intermediary core layer 104.

In various embodiments, rubber layer 106 is a permanent rubber adhesive applied to a first side of the intermediary core layer 104. In some embodiments, rubber layer 106 is a pressure sensitive rubber adhesive. Rubber layer 106 may be aggressive enough to adhere to a surface with low surface energy, such as protective cover 120. Rubber layer 106 may be applied to protective cover 120 via lamination to the cover. In various embodiments, cover 120 may be fabricated from a low surface energy plastic film, such as low density polyurethane (LDPE) plastic. Protective cover 200 is further described with reference to FIGS. 2A and 2B.

In some embodiments, the pressure sensitive rubber adhesive of rubber layer 106 may comprise a styrene-butadiene-styrene (SBS) block copolymer. The rubber adhesive may comprise a higher carbon-carbon double bond content primarily due to higher aromatic ring content (from styrene), as well as C5 aliphatic tackifier resin (i.e. cis/trans-1,3-pentadiene and cyclopentene).

In some embodiments, rubber layer 106 may include a peel adhesion of approximately 107 ounces per inch (oz/in), or 6.7 pound-force per inch (lbf/in). In some embodiments, rubber layer 106 may include a peel adhesion of approximately 100 to 120 ounces per inch (oz/in). In yet other embodiments, the rubber layer 106 may include a peel adhesion of at least 90 oz/in or higher. A rubber layer with a peel adhesion of lower than 90 oz/in may result in adhesive confusion, making it difficult to remove the liner, or causing the rubber layer 106 to completely delaminate from cover 200 during cover removal. Such peel force may be measured based on a 180 degree peel test to a standard steel panel using test standard ASTM D-3330-STD 10 from the American Section of the International Association for Testing Materials, or the test standard PSTC-101 from the Pressure Sensitive Tape Council.

In various embodiments, acrylic layer 108 is a removable acrylic adhesive applied to an opposite second side of the intermediary core layer 104. FIG. 1A shows a differential adhesive system prior to application on a desired surface 300. As such, adhesive system 100 in FIG. 1A includes liner layer 130 covering acrylic layer 108. In various embodiments, liner layer 130 is configured to protect the adhesive characteristics of acrylic layer 108. In various embodiments, liner layer 130 may comprise a polyester film, such as polyethylene terephthalate (PET), polypropylene, polyethylene, etc. In other embodiments, liner layer 130 may comprise a paper release liner, such as glassine paper, super calendared kraft paper, clay coated kraft paper, etc. In some embodiments, liner layer 130 may include a low surface energy release coating such as a crosslinked silicone layer. In some embodiments, liner layer 130 may include a cured coating to further protect acrylic layer 108 from ultraviolet (UV) radiation. In some embodiments, liner layer 130 may be oversized with one or more dimensions being greater than the dimensions of differential adhesive 102. Such oversized configuration allows for easier removal of liner layer 130. In some embodiments, liner layer 130 may be marked or otherwise colored differently from that of cover 120 for increased visibility of the location of adhesive 102. The coloring techniques are advantageous, because it reduces user efforts and the total number of users required (e.g., in a hospital setting where the total number of available medical professionals is limited) to locate the adhesive and to place the cover on a medical device.

FIG. 1B shows a differential adhesive system applied to a desired surface 300. Acrylic layer 108 may be configured to removably adhere to surface 300. Surface 300 may be the surface of a device. In various embodiments, the device may be medical equipment (large stationary machinery), such as a CT scanner or MRI machine, etc. However, in some embodiments, the device may be smaller machinery, such as computer screens, control panels, mobile machinery, overhead lights, lamps, hand-held equipment such as surgical tools, etc. In some embodiments, surface 300 comprise a painted metal or plastic surface. In some embodiments, surface 300 may be a textured surface.

In some embodiments, acrylic layer 108 is a pressure sensitive acrylic adhesive. In some embodiments, acrylic layer 108 includes a "medium level of adhesion" as defined by a peel force to a stainless steel panel using test standard ASTM D-3330-STD 10 from the American Section of the International Association for Testing Materials, or the test standard PSTC-101 from the Pressure Sensitive Tape Council. For example, particular example embodiments, of acrylic layer 108 may include a peel adhesion of approximately 40 to 60 ounces per inch (oz/in) according to ASTM D-3330-STD 10-180 degree-12" per minute to stainless steel, or according to PSTC-101-180 degree peel test to standard steel panel. In some embodiments, acrylic layer 108 may include a peel adhesion of approximately 51 oz/in, or 3.2 lbf/in. Acrylic adhesives with a peel adhesion of less than 40 oz/in may not possess sufficient bond strength to secure a cover a certain weight and size on the surface of a device. Acrylic adhesives with a peel adhesion of greater than 60 oz/in may be too aggressive and leave residual adhesive when removed from the surface of a device.

In some embodiments, acrylic layer 108 may comprise a thermoset cross-linked acrylic adhesive. The cross-linked configuration may allow acrylic layer 108 to maintain its structural integrity and prevent cracks and splits in layer 108 during removal from surface 300, preventing residue from being left behind on surface 300. However, in other embodiments, the acrylic adhesive may not be crosslinked. In some embodiments, an acrylic adhesive that is not crosslinked may include a higher glass transition temperature than an acrylic adhesive that is crosslinked. Acrylic layer 108 may exhibit carbonyl characteristics and/or alkyl characteristics.

In various embodiments, differential adhesive system 100 maintains its adhesive properties for a desired period of time. For example, adhesive system 100 may maintain its adhesive properties for at least 40 days when stored at 50° F.-80° F. (10° C.-27° C.) and at a relative humidity of 40-60 percent. The described adhesives also provide a more cost-effective solution than various silicone adhesives.

Device Cover

Figure 2B:
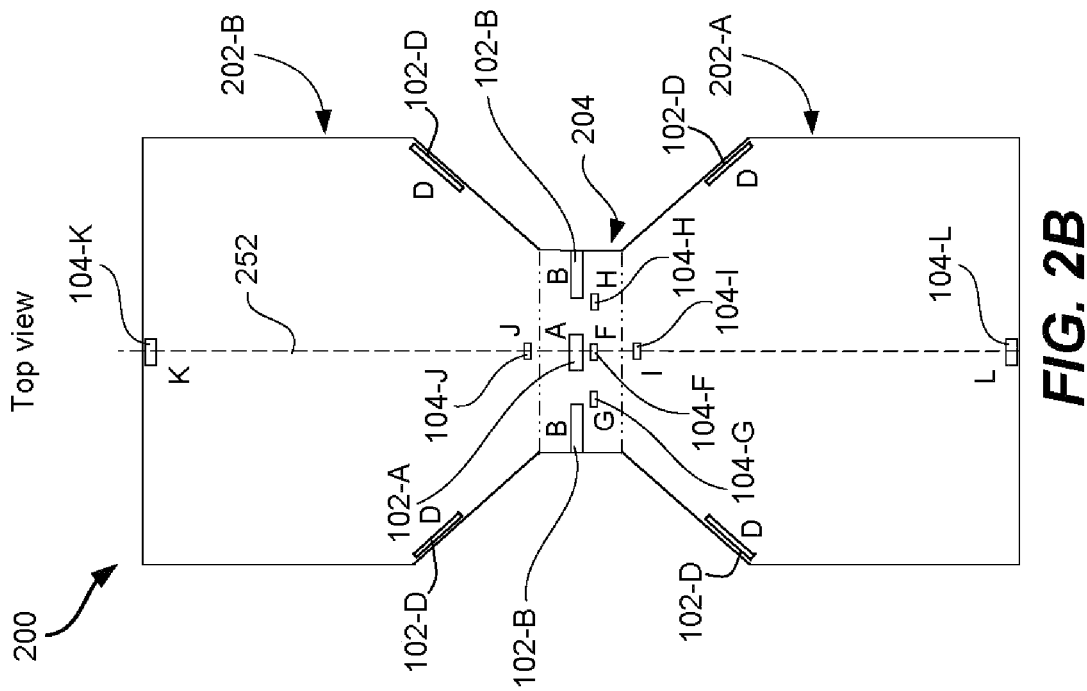
FIGS. 2A and 2B illustrate an example device cover in accordance with various embodiments of the present disclosure.
Figure 2A:
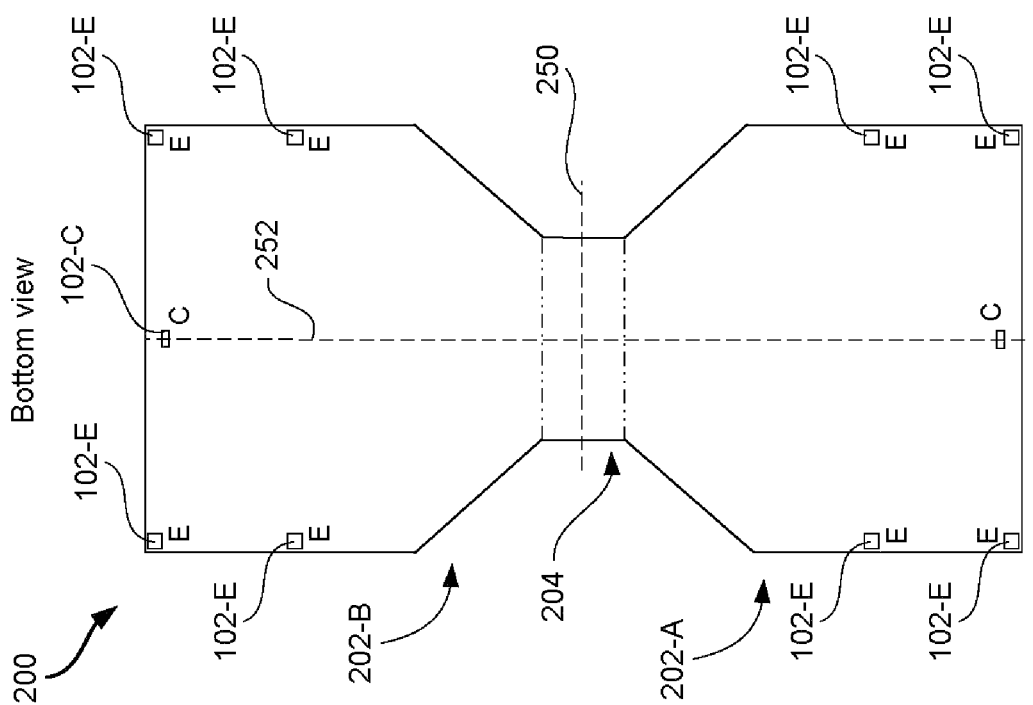

As previously described, adhesive system 100 includes a cover 120 with differential adhesive 102. In some embodiments, cover 120 may include one or more patches or strips of differential adhesive 102. FIGS. 2A and 2B illustrate an example device cover 200 that may be implemented with various embodiments of the present disclosure. As used herein, the term "Gantry Guard" or "Gantry Guard Flex" may be used to interchangeably with device cover 200. In various embodiments, device cover 200 may be cover 120. FIG. 2A depicts a bottom view of cover 200, while FIG. 2B depicts a top view of cover 200.

Protective cover 200 may comprise various flexible or rigid plastic or plastic-like materials. In various described embodiments, protective cover 200 may be a waterproof or water resistant material. For example, protective cover 200 may comprise various plastic materials, including polyvinyl film, polyurethane, polyethylene, etc. In an example embodiment, protective cover 200 is fabricated from low density polyethylene (LDPE) plastic.

In another example use, the plastic cover with integrated pressure sensitive adhesive can be used for covering parts during product manufacture or maintenance where prolonged but temporary use of a cover is needed, and where the adhesive needs to remove cleanly from the surface. For instance, currently, vehicle frames are covered with woven barriers during manufacture, and plastic coverings are taped onto the vehicle frames during body work. Woven barriers are generally more expensive than plastic barriers. Furthermore, the costs for labor and time for the taping of such plastic coverings would be greatly reduced. Various examples of such adhesives are further described in U.S. patent application Ser. No. 15/963,934, entitled Removable Adhesive for Device Coverings filed on Apr. 26, 2018, which application is incorporated by reference herein in its entirety and for all purposes.

In an example embodiment, cover 200 may include a tensile property durable enough to withstand the weight of secretions or fluids up to 2.5 pounds. However, cover 200 may be configured to withstand greater or lesser weight depending on various user requirements. Such tensile properties may be measured according to ASTM D882 standards.

In an example embodiment, cover 200 is translucent such that device patient positioning colored lasers, or other optical mechanisms, can transmit clearly through the cover. In some embodiments, cover 200 is additionally configured to be radiolucent or transparent in images captured by the device, and do not affect image quality. As such, cover 200 would allow for an artifact-free image without requiring increased radiation during operation, thereby preventing increased patient radiation dosage.

In some embodiments, the cover 200 is sterilizable, because, the cover 200, as well as other medical devices or equipment may be reused after coming in contact with a patient (e.g., the patient's person or her blood or bodily fluids) and be reused. The cover 200 may be sterilized by heat (dry heat or autoclave/steam), pressure, chemicals, or irradiation. In some embodiments, the cover 200 is made of plastic and other materials that are suitable for sterilization by disinfectant chemicals, such as bleach, ethanol, isopropyl alcohol, iodine, and hydrogen peroxide.

Protective cover 200 may be a cover configured to create a protective barrier against fluids and other debris from damaging or soiling a device, such as Computed Tomography (CT) machines, Magnetic Resonance Imaging (MRI) machines, or other imaging devices. Protective cover 200 may additionally or alternatively function to create a sterile barrier between a patient and the device. As such, protective cover 200 may protect valuable equipment from potential damage and decrease clean-up time when fluid spills or issues occur. For example, cover 200 may provide protection against viral penetration as measured using ASTM F1671/F167M-13 Standard Test Method for Resistance of Materials Used in Protective Clothing to Penetration by Blood-Borne Pathogens Using Phi-X174 Bacteriophage Penetration as a Test System.

For example, protective cover 200 may be configured to line the interior of an imaging device. As another example, protective cover 200 may be configured to protect the bottom of a CT gantry (center opening) and scanner from fluids that may enter into the imaging window or spill down the front table side of the scanner or back non-table side of the scanner. This will protect valuable equipment from potential damage and decrease clean-up time when fluid spills or issues do occur. In various embodiments, protective cover 200 may be a cover configured to line various other devices, such as gurneys, operating tables, examination chairs and benches, etc. In some embodiments, protective cover 200 may be configured to cover the exterior surface of various devices and/or equipment to protect from dust, fluids, and debris.

In various embodiments cover 200 may include a symmetrical shape, as depicted, to provide equal coverage of both table and non-table sides of a device, such as a CT scanner. Cover 200 may be a universal cover configured to fit one or more CT scanner approved by the U.S. Food and Drug Administration (FDA). Cover 200 may include an extended drape size to provide full protection to both the table and non-table sides of the bottom of the CT gantry opening and scanner. Coverage may extend to the floor, reducing fluids getting under the scanner or on foot pedals. Cover 200 may be optimized to correct poor adherence to an inner bore of the CT scanner during installation. Cover 200 may also be configured to be folded in a manner for faster and easier unfolding than original covers. Folding technique changed to correct poor adherence to inner bore during installation.

In an example embodiment, cover 200 may include two symmetrical drape sections, 202-A and 202-B, extending from a bore section 204. Each drape section may extend from the bore section at an angle. For example, a first edge of a drape section may extend from the bore section at a 50 degree angle from a horizontal axis 250. A second edge of the drape section may extend from the bore section at an opposite 50 degree angle from a horizontal axis 250. The angled dimension (e.g., the 50 degree) is technically advantageous, because it keeps the drape section closer to the outer surface of a medical device without requiring additional adhesive for this purpose.

Each drape section may be symmetrical across the horizontal axis 250 and/or a vertical axis 252. The total length of cover 200 may be approximately 170 inches with each drape section extending approximately 77 inches and the bore section extending approximately 16 inches of the total length. The total width of the widest portion of each drape section may be approximately 82 inches, while the corresponding dimension of the narrower bore section extends approximately 39 inches.

The symmetrical shape provides equal coverage to both table and non-table sides of a CT scanner. The extended drape size may also provide full protection to both the table and non-table side of the bottom of the CT gantry opening and scanner. Coverage can extend to the floor, reducing fluids getting under the scanner or on foot pedals. In some embodiments, the cover may include drape sections with different lengths. Such drape sections may still allow for coverage to the scanner, floor, and foot pedals. In other embodiments, the cover may include drape and bore sections of various different lengths and measurements. Further, the symmetrical shape makes it easier to apply or place the cover on a medical device, because when the cover has a consistent density, having a symmetrical shape makes a device consistent in weight and thus easier to apply or place on a medical device with reduced user efforts. The cover 200 may be configured with one or more adhesives, such as adhesives 102 to removably secure cover 200 to a device, such as a CT scanner. As illustrated in FIGS. 2A and 2B, cover 200 includes one or more tabs or strips of adhesives 102-A, 102-B, 102-C, 102-D, and 102-E. Each of these described adhesives may be adhesive 102 with particular dimensions. From the top view of cover 200, adhesive 102-A is located at location A at the center of the bore section, adhesives 102-B is located at locations B to the left and right of adhesive 102-A on the bore section, and adhesive 102-D is located at locations D near the angled edges of each of the drape sections. From the bottom view of cover 200, adhesives 102-C are located at locations C on the drape sections, while adhesives 102-E are located at locations E on the drape sections. The locations of adhesives shown in FIGS. 2A and 2B are exemplary, and in various embodiments, the described adhesives may be configured to be located on various other portions of cover 200. Such configuration of adhesives on cover 200 may securely attach cover 200 to the surface of a device for at least 24 hours.

In some embodiments, such adhesives allow cover 200 to be adhered to the CT gantry bore during an imaging procedure. In some embodiments, cover 200 may include additional optional adhesive tabs or strips to allow for customizable protection based on the configuration of the device. For example, additional adhesive tabs may allow the cover to be pulled back over itself to improve fit or increase security of attachment to the device. For another example, a medical device cover may include 10 adhesive strips at various corners of the cover and a medical professional may, in some instance, apply only 3 of the total 10 adhesive strips to affix the cover to a nearby gurney, forming in a triangle shape protective layer, and in some other instances, apply 8 of the total 10 adhesive strips to affix the cover in a triangle shape to a nearby CT machine, forming a square shape protection layer. Different shapes of protection layers can be used to contain different types or amount of fluid contaminations (e.g., serious vomit or urine contamination and normal sweating).

In some embodiments, the size of adhesive tabs or strips may be increased or the number of adhesive tabs or strips may be decrease to allow for faster application. In some embodiments, optional adhesive tabs or strips may be positioned on other portions of cover 200 to allow for customizable shape and attachment according to the particular device or user's requirements. In some embodiments, adhesives may be covered with a colored liner layer, such as liner 130 for easier identification, location, and differentiation from other labeling on cover 200. As previously described, such liner 130 may be oversized to create a section not secured to the adhesive to provide for convenient removal of the liner. For example, each side of the liner may be sized to be 0.50 inches greater than each side of the respective adhesive tab or strip that it covers.

Figure 2C:
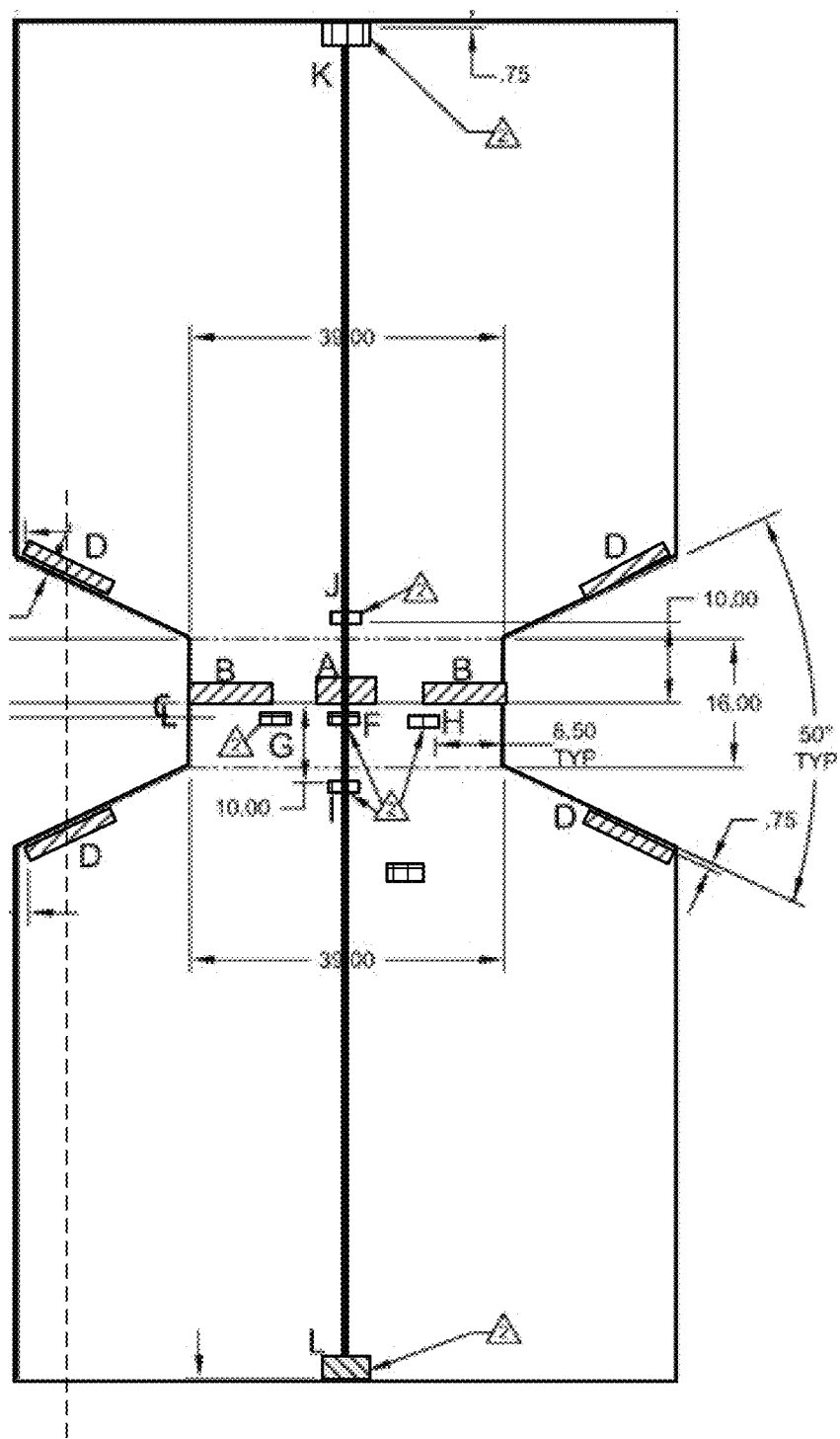
FIGS. 2C and 2D illustrate another top view of an example device cover and its associated instruction labels and measurements, respectively, in accordance with various embodiments of the present disclosure.
Figure 2D:
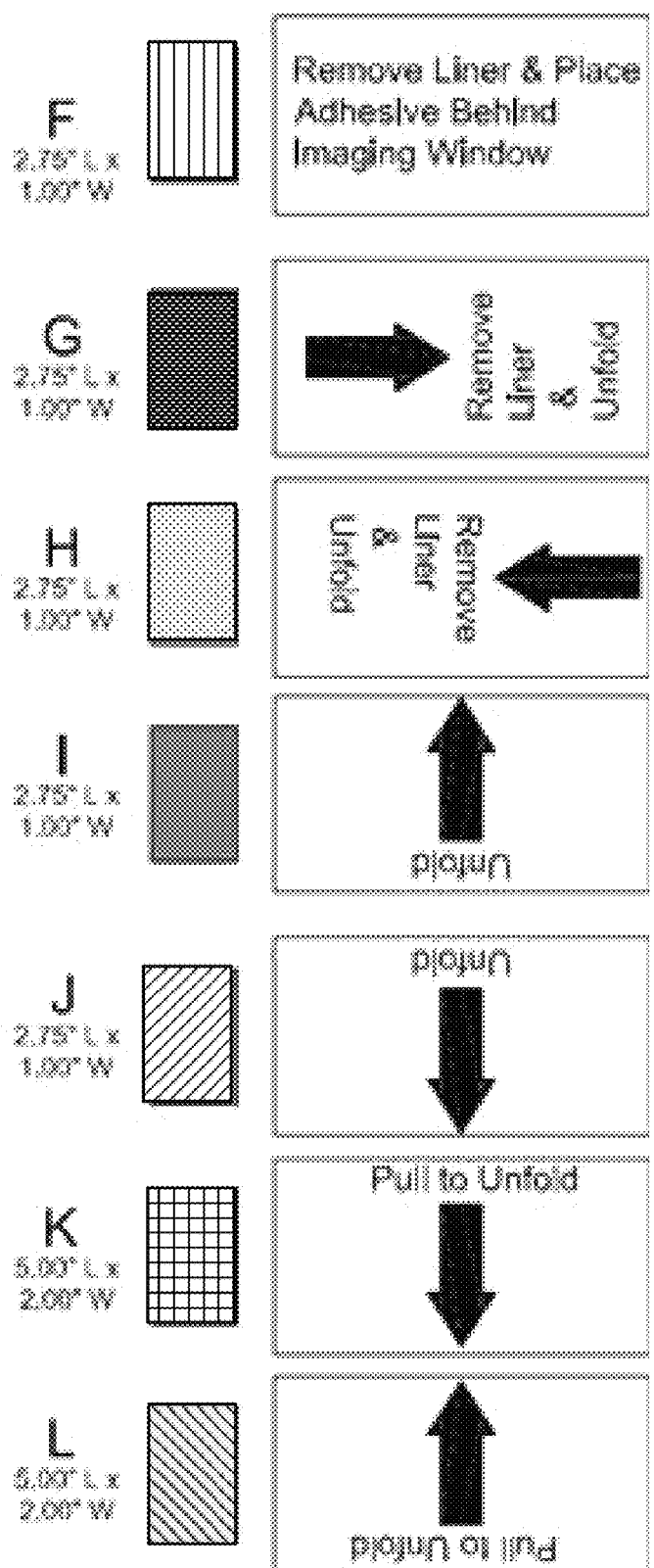

Such labeling may include application instruction labels 104-F, 104-G, 104-H, 104-I, 104-J, 104-K, and 104-L, at locations F, G, H, I, J, K, and L, respectively, as shown in FIGS. 2A, 2B, and 2C. FIGS. 2C and 2D illustrate another example top view of a device cover and associated instruction labels and measurements, in accordance with various embodiments of the present disclosure. Such instructions labels may guide a user to position and secure device cover 200 onto a device, such as a CT scanner. In some embodiments, the instructions labels provide a folding technique optimized to correct poor adherence to the inner bore during installation. The folding technique may also allow for faster and easier unfolding than existing covers.

In FIG. 2C, the positions of adhesives 102-A, 102-B, and 102-D, as well as instruction labels 104-F, 104-G, 104-H, 104-I, 104-J, 104-K, and 104-L, are shown, as described in FIGS. 2A and 2B. For example, as shown in FIG. 2D, label 104-F indicates instructions to "Remove Liner & Place Adhesive Behind Imaging Window." Label 104-G indicates instructions to "Remove Liner & Unfold" with an arrow indicating the direction to unfold. Label 104-H indicates instructions to "Remove Liner & Unfold" with an arrow indicating the direction to unfold. Labels 104-I and 104-J indicate instructions to "Unfold" with respective arrows indicating the direction to unfold. Labels 104-K and 104-L indicate instructions to "Pull to Unfold" with respective arrows indicating the direction to unfold. In particular embodiments, the instruction labels may range from 2.75 inches by 1.00 inches to 5.00 inches by 2.00 inches. However, in various embodiments, instruction labels may be configured with various different dimensions depending on design requirements, visibility, or organization. Further instructions for applying a device cover onto a device, such as a CT scanner, are described in the method of operation below.

Method of Operation

Figure 3A:
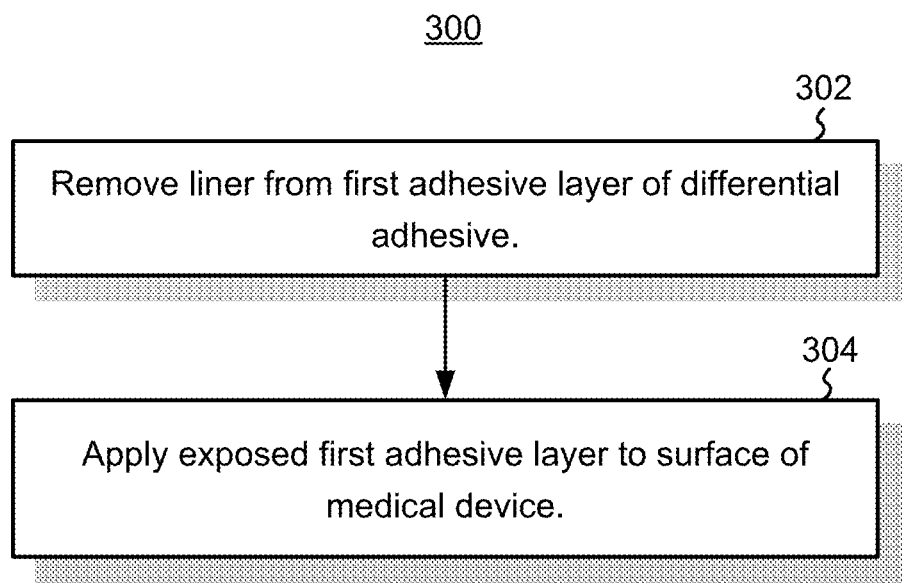
FIG. 3A illustrates an example method for operating a differential adhesive to attach a device cover to a surface of a device, in accordance with various embodiments of the present disclosure.

FIG. 3A illustrates an example method 300 for operating a differential adhesive to attach a device cover to a surface of a device, in accordance with one or more embodiments. In various embodiments, the device cover is cover 200 with one or more adhesive strips or tabs, as described herein. Method 300 may comprise removing (302) a liner from a first adhesive layer of a differential adhesive, such as differential adhesive 102. For example, the liner may be liner 130 and the first adhesive layer may be acrylic layer 108. The method 300 may then comprise applying (304) the first adhesive layer to the surface of a device, such as a CT scanner, for instance.

Figure 3B:
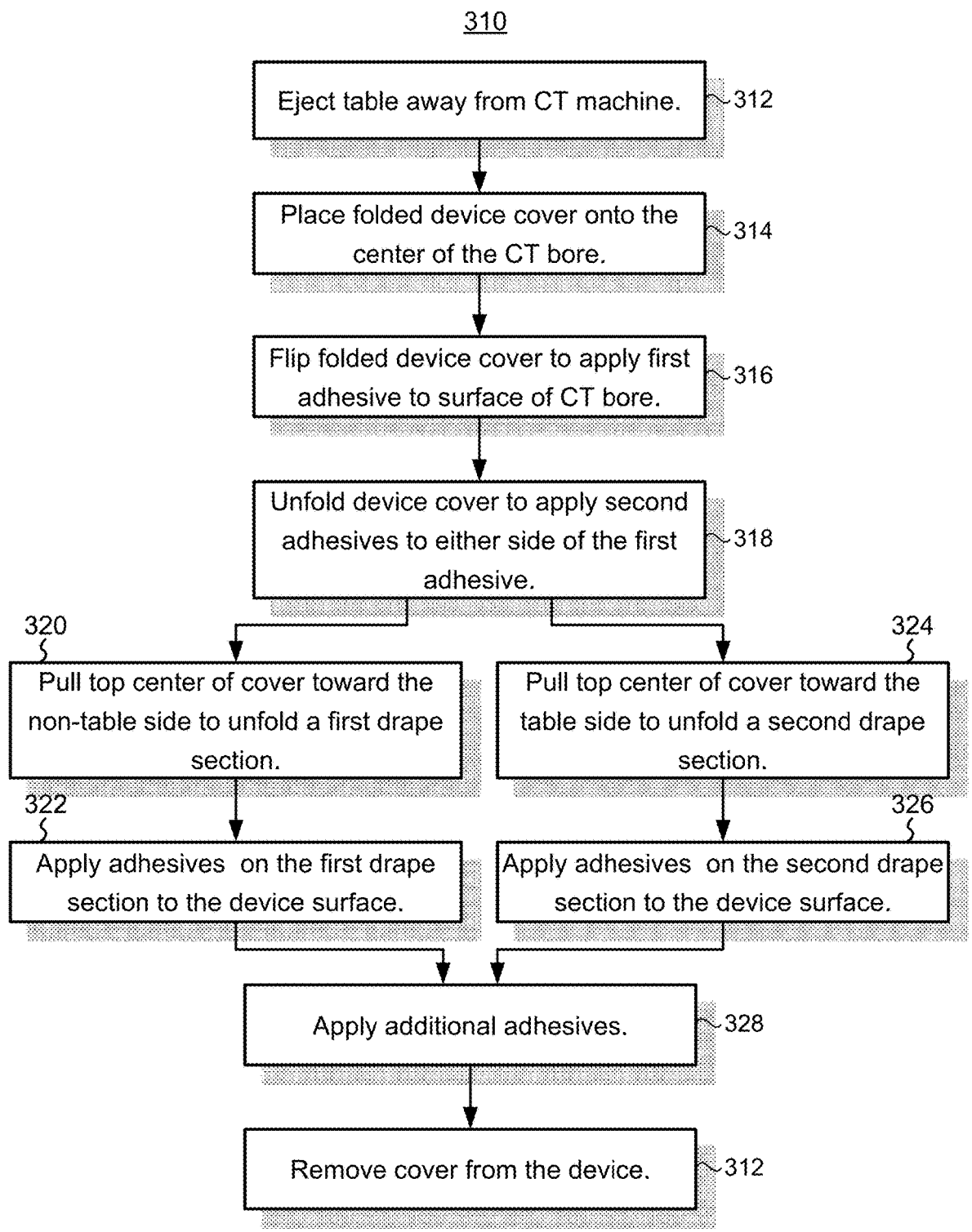
FIG. 3B illustrates an example method for protecting a device using a device cover, in accordance with various embodiments of the present disclosure.

FIG. 3B illustrates an example method 310 for protecting a device using a device cover, such as cover 200, in accordance with various embodiments of the present disclosure. In some embodiments, the device cover may be implemented on a CT scanner in method 310. However, one or more steps of method 310 may be applied to other devices, including but not limited to MRI scanners and other devices.

At step 312, the table of a CT scanner may be ejected. This may provide increased access or maneuverability for a user, such as a technician or technologist, to apply the device cover onto the CT scanner. In some embodiments, step 312 is an optional step which may not be performed. At step 314, the cover may be placed in the center of the CT bore.

The following steps 316-322 may be implemented with the user on the non-table side of the CT scanner. At step 316, the cover may be flipped over to apply adhesive 102-A to the center of the CT bore surface. For example, following instruction label 104-F, a liner, such as liner 130, is removed from adhesive 102-A, as described in method 300. The cover may then be flipped over so that the adhesive 102-A is facing the surface of the CT bore, and the cover may be pressed to the center of the bore such that adhesive 102-A forms an adhesive contact with the surface of the device at the center of the bore. In some embodiments, it is preferred that the adhesive is not applied to the imaging window. In some embodiments, it is preferred that the adhesive is applied behind the imaging window.

At step 318, portions of the cover may be unfolded to apply the two adhesives 102-B to the surface of the CT bore on the right and left sides of adhesive 102-A. For example, following instruction label 104-G, a liner may be removed from a first adhesive 102-B and the portion of the cover with the first adhesive 102-B may be unfolded such that the first adhesive 102-B is facing the surface of the CT bore to the left side of adhesive 102-A. The first adhesive 102-B may then be pressed to the surface of the CT bore to form an adhesive contact with the surface. Then, following instruction label 104-H, the liner of a second adhesive 102-B may be removed, and the portion of the cover with the second adhesive 102-B may be unfolded such that the second adhesive 102-B is facing the surface of the CT bore to the right side of adhesive 102-A. The second adhesive 102-B may then be pressed to the surface of the CT bore to form an adhesive contact with the surface. It should be recognized that the first adhesive 102-B may be positioned to the right of adhesive 102-A, while the second adhesive 102-B may be positioned to the left of adhesive 102-A, with no difference in functionality, depending on the configuration and initial positioning of the cover.

At step 320, the top center of the cover may be pulled towards the non-table side to unfold a first drape section 202-A. For example, following instruction label 104-I, drape section 202-A may be completely unfolded to cover the non-table side of the CT scanner. At this point, the top view of drape section 202-A is facing down. At step 322, the left and right sides of drape section 202-A may be adhered to the CT scanner using the adhesives 102-D located on drape section 202-A. The liners of such adhesives 102-D may be removed and the adhesives 102-D may be pressed against the device surface to form an adhesive contact.

Steps 324 and 326 may be implemented with the user at the table side of the CT scanner. At step 324, additional material at the top center of the cover may be pulled toward the table side to unfold a second drape section 202-B. For example, following instruction label 104-J, drape section 202-B may be complete unfolded to cover the table side of the CT scanner. At step 326, the left and right sides of drape section 202-B may be adhered to the CT scanner using the adhesives 102-D located on drape section 202-B. The liners of such adhesives 102-D may be removed and the adhesives 102-D may be pressed against the device surface to form an adhesive contact.

At step 328, additional adhesives 102-E located on drape sections 202-A and 202-B may be applied to gather excess material or to minimize the amount of plastic on the floor. For example, adhesive strips 102-E may be placed against the cover itself or against the floor, the device, or against other components of the device, such as foot pedals, or underside of the table. In some embodiments, step 328 is an optional step which may not be performed.

At step 330, the cover is removed from the device. In some embodiments, step 330 may be performed after operation of the device in an exam or procedure. For example, the cover may be pulled from the back of the device to separate the adhesives from the device until completely removed. In some embodiments, it may be desired to avoid pulling the cover from the center to avoid tearing of the cover.

Figure 4:
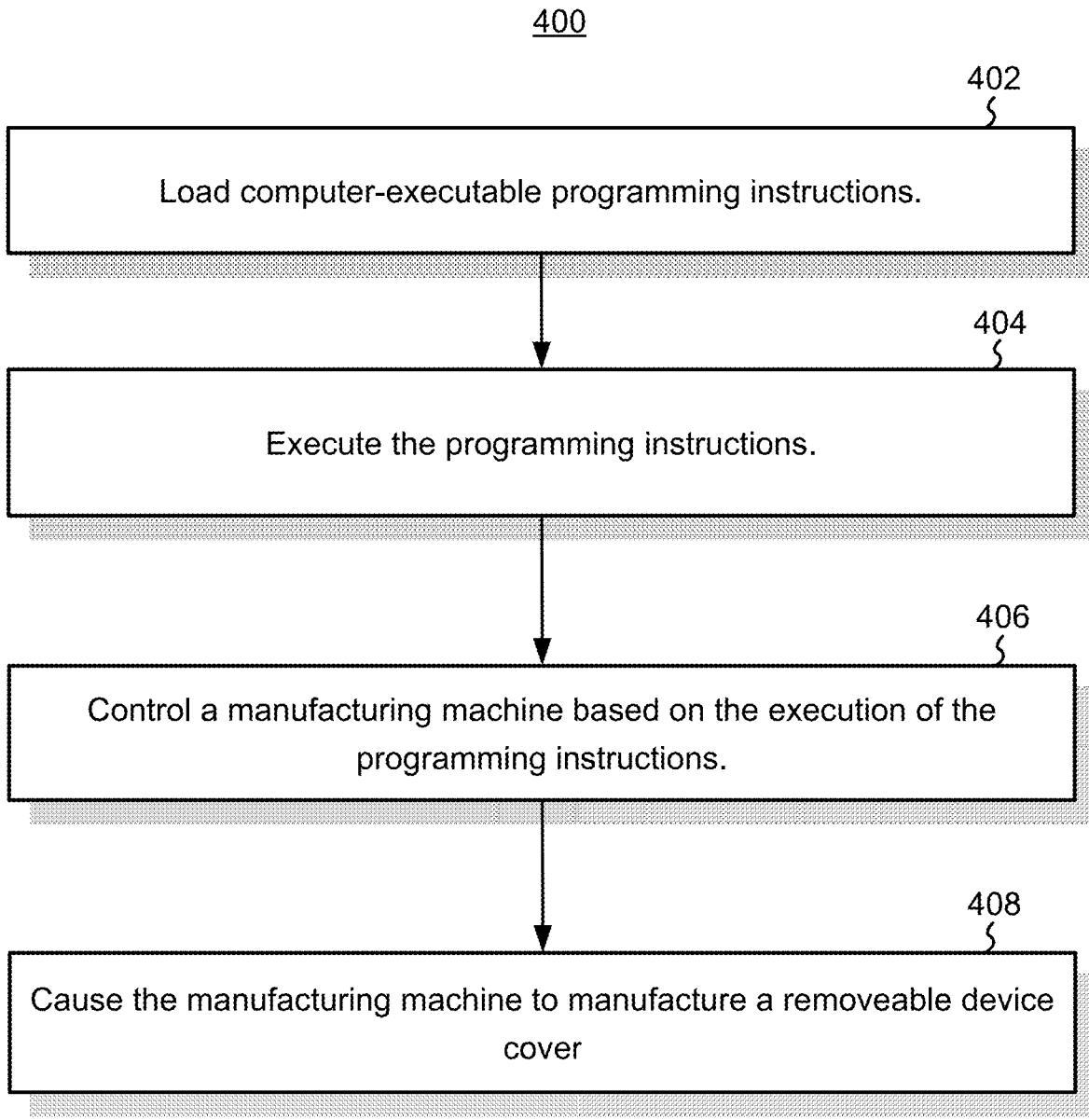
FIG. 4 is a flowchart illustrating an example computer-implemented method for manufacturing a differential adhesive in accordance with various embodiments of the present disclosure.

FIG. 4 is a flowchart illustrating an example computer-implemented method 400 for manufacturing a removable device cover. The computer system 500, when properly programmed, can execute the method 400.

In various implementations, the method 400 includes using a computer to load (402) computer-executable programming instructions from a non-volatile memory of the computer to a volatile memory of the computer. After loading the programming instructions, the computer may execute (404) the programming instructions using the volatile memory.

Based on the execution of the programming instructions, the computer may control (406) a manufacturing machine, for example, a cutting machine, a molding machine, or a pressing machine. By controlling the manufacturing machine, the computer causes (408) the manufacturing machine to manufacture a differential adhesive as described in one or more of the implementations disclosed in the present disclosure. By controlling the manufacturing machine, the computer may further cause (410) the manufacturing machine to apply the differential adhesive as described onto a device cover as described. For example, the rubber layer 106 may be applied to the device cover 200 to permanently secure adhesive 102 to cover 200.

Figure 5:
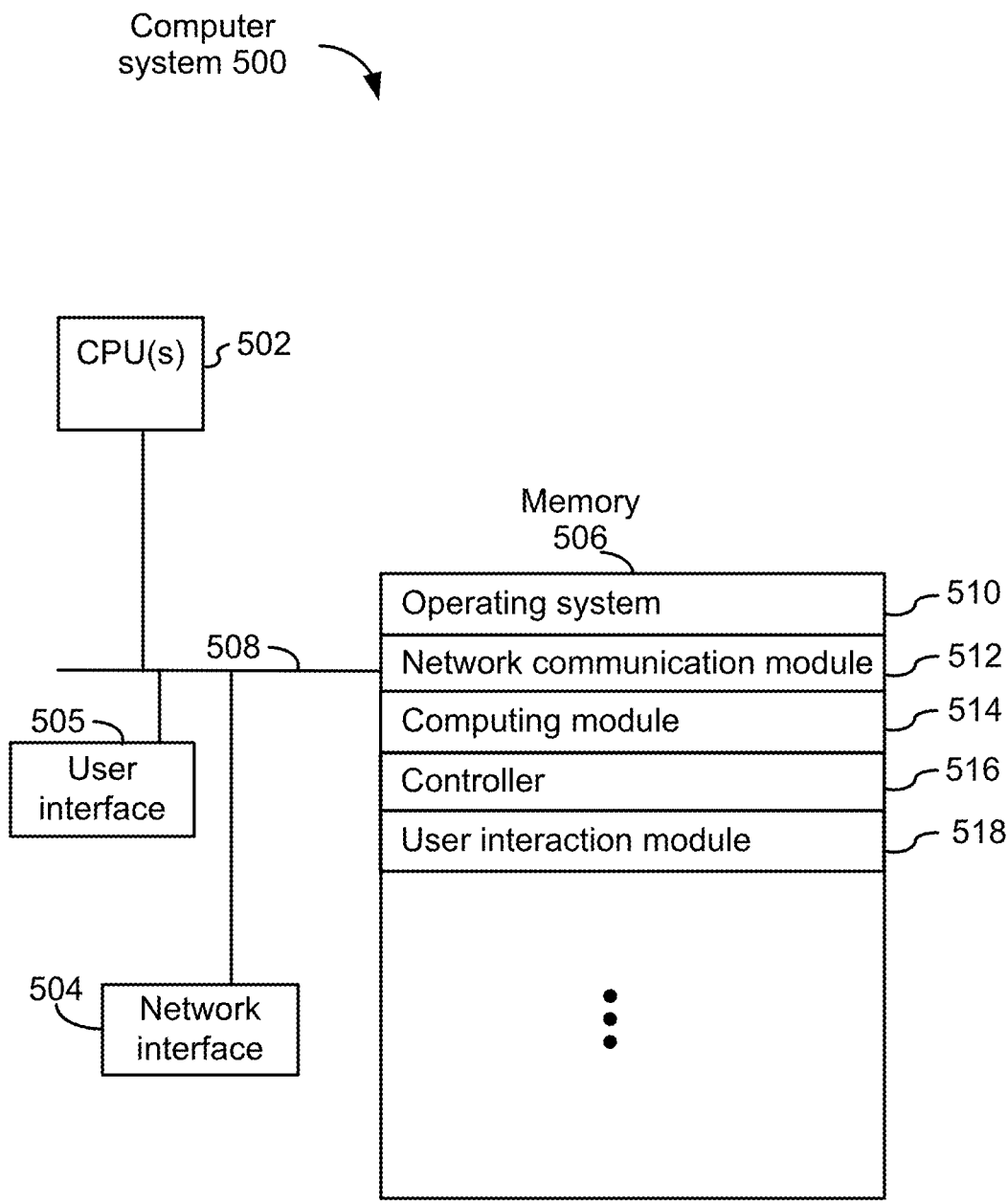
FIG. 5 is a block diagram illustrating an example computer system for manufacturing a differential adhesive in accordance with various embodiments of the present disclosure.
Figure 6A:
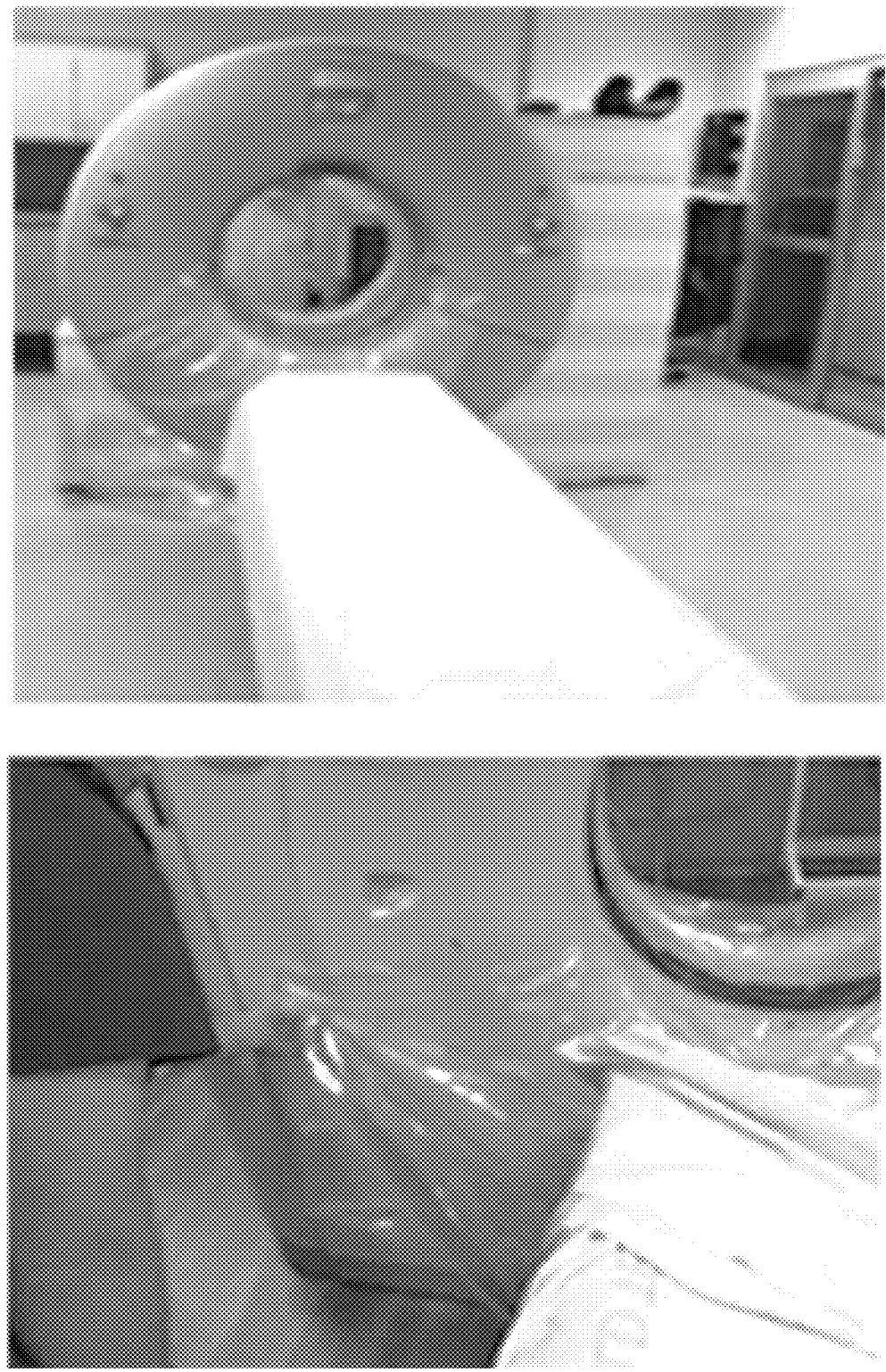
FIGS. 6A-6C are photo images illustrating how an example device cover may be used with a medical device in accordance with various embodiments of the present disclosure.
Figure 6B:
Figure 6B:
Figure 6C:
Figure 6C:

FIG. 5 is a block diagram illustrating an example computer system 500 for manufacturing a device cover. The computer system 500 in some implementations includes one or more processing units CPU(s) 502 (also referred to as processors), one or more network interfaces, optionally a user interface, a memory 506, and one or more communication buses 508 for interconnecting these components. The communication buses 508 optionally include circuitry (sometimes called a chipset) that interconnects and controls communications between system components. The memory 506 typically includes high-speed random access memory, such as DRAM, SRAM, DDR RAM or other random access solid state memory devices; and optionally includes non-volatile memory, such as one or more magnetic disk storage devices, optical disk storage devices, flash memory devices, or other non-volatile solid state storage devices. The memory 506 optionally includes one or more storage devices remotely located from the CPU(s) 502. The memory 506, or alternatively the non-volatile memory device(s) within the memory 506, comprises a non-transitory computer readable storage medium. In some implementations, the memory 506 or alternatively the non-transitory computer readable storage medium stores the following programs, modules and data structures, or a subset thereof:

- an operating system 510 (e.g., an embedded Linux operating system), which includes procedures for handling various basic system services and for performing hardware dependent tasks;
- a network communication module 512 for connecting the computer system with a manufacturing machine via one or more network interfaces (wired or wireless);
- a computing module 514 for executing programming instructions;
- a controller 516 for controlling a manufacturing machine in accordance with the execution of programming instructions; and
- a user interaction module 518 for enabling a user to interact with the computer system 500.

One or more of the above identified elements may be stored in one or more of the previously mentioned memory devices, and correspond to a set of instructions for performing a function described above. The above identified modules or programs (e.g., sets of instructions) need not be implemented as separate software programs, procedures or modules, and thus various subsets of these modules may be combined or otherwise re-arranged in various implementations. In some implementations, the memory optionally stores a subset of the modules and data structures identified above. Furthermore, the memory may store additional modules and data structures not described above.

Plural instances may be provided for components, operations or structures described herein as a single instance. Finally, boundaries between various components, operations, and data stores are somewhat arbitrary, and particular operations are illustrated in the context of specific illustrative configurations. Other allocations of functionality are envisioned and may fall within the scope of the implementation(s). In general, structures and functionality presented as separate components in the example configurations may be implemented as a combined structure or component. Similarly, structures and functionality presented as a single component may be implemented as separate components. These and other variations, modifications, additions, and improvements fall within the scope of the implementation(s).

It will also be understood that, although the terms "first," "second," etc. may be used herein to describe various elements, these elements should not be limited by these terms. These terms are only used to distinguish one element from another. For example, a first adhesive layer could be termed a second adhesive layer, and, similarly, a second adhesive layer could be termed a first adhesive layer, without changing the meaning of the description, so long as all occurrences of the "first adhesive layer" are renamed consistently and all occurrences of the "second adhesive layer" are renamed consistently. The first adhesive layer and the second adhesive layer are both adhesive layers, but they are not the same adhesive layer.

The terminology used herein is for the purpose of describing particular implementations only and is not intended to be limiting of the claims. As used in the description of the implementations and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in accordance with a determination" or "in response to detecting," that a stated condition precedent is true, depending on the context. Similarly, the phrase "if it is determined (that a stated condition precedent is true)" or "if (a stated condition precedent is true)" or "when (a stated condition precedent is true)" may be construed to mean "upon determining" or "in response to determining" or "in accordance with a determination" or "upon detecting" or "in response to detecting" that the stated condition precedent is true, depending on the context.

The foregoing description included example systems, methods, techniques, instruction sequences, and computing machine program products that embody illustrative implementations. For purposes of explanation, numerous specific details were set forth in order to provide an understanding of various implementations of the inventive subject matter. It will be evident, however, to those skilled in the art that implementations of the inventive subject matter may be practiced without these specific details. In general, well-known instruction instances, protocols, structures and techniques have not been shown in detail.

The foregoing description, for purpose of explanation, has been described with reference to specific implementations. However, the illustrative discussions above are not intended to be exhaustive or to limit the implementations to the precise forms disclosed. Many modifications and variations are possible in view of the above teachings. The implementations were chosen and described in order to best explain the principles and their practical applications, to thereby enable others skilled in the art to best utilize the implementations and various implementations with various modifications as are suited to the particular use contemplated.

What is claimed is:

1. A device cover comprising:
   a bore section;
   a first drape section extending from a first end of the bore section,
      wherein a first edge of the first drape section extends from the first end of the bore section, and
   a second drape section extending from a second end of the bore section,
      wherein the first drape section and second drape section are symmetrical with respect to each other about both a horizontal axis of the device cover and a vertical axis of the device cover, such that there is a 50° angle between the first edge on the first drape section and a corresponding edge on the second drape section; and
      wherein a width of a widest portion of each of the first drape section and the second drape section is greater than any width of the bore section.

2. The device cover of claim 1, further comprising one or more adhesive tabs, each adhesive tabs comprising:
   an intermediary body having a first side and an opposite second side;
   a first adhesive layer attached to the first side, the first adhesive layer comprising an acrylic adhesive; and
   a second adhesive layer attached to the second side, the second adhesive layer comprising a rubber adhesive secured to the device cover.

3. The device cover of claim 2, wherein the first adhesive layer of each adhesive tab is covered by a liner layer, wherein the dimension of each side of the liner layer is greater than the dimension of each side of the corresponding differential adhesive.

4. The device cover of claim 3, further comprising one or more instruction labels including instructions for operating the device cover, wherein the instruction labels are of a different color than the liner layers.

5. The device cover of claim 2, wherein the one or more adhesive tabs are located on one or more of the following: the bore section, the first drape section, and the second drape section.

6. The device cover of claim 2, wherein a first set of the one or more adhesive tabs are configured for releasably attaching the device cover to a surface of a first object, and wherein a second set of the one or more adhesive tabs are configured for releasably attaching the device cover to a surface of a second object.

7. The device cover of claim 2, wherein the intermediary body comprises a polyester film.

8. The device cover of claim 2, wherein the acrylic adhesive of the first adhesive layer includes a peel adhesion of 40 ounces per inch to 60 ounces per inch.

9. The device cover of claim 2, wherein the acrylic adhesive of the first adhesive layer comprises a cross-linked pressure sensitive acrylic adhesive.

10. The device cover of claim 2, wherein the first adhesive layer is configured for releasable attachment to the surface of a first object.

11. The device cover of claim 10, wherein the first object is a CT scanner.

12. The device cover of claim 2, wherein the second adhesive layer is configured for permanent attachment to the device cover.

13. The device cover of claim 1, wherein the device cover comprises a covering of plastic material.

14. The device cover of claim 1, wherein the device cover comprises a polyethylene film.

15. The device cover of claim 1, wherein the bore section is configured to fit within the bore of a computed tomography (CT) scanner.

16. The device cover of claim 1, wherein the device cover is radiolucent.

17. The device cover of claim 1, wherein the device cover is sterilizable.

18. A method of attaching the device cover of claim 1 to a surface of a device, the method comprising:
    placing the bore section of the device cover at the center of a bore of the device;
    unfolding the first drape section;
    unfolding the second drape section.

19. The method of claim 18, further comprising:
    removing a liner layer from an adhesive tab secured to the device cover,
    applying the exposed adhesive tab to the surface of the device.

20. The method of claim 19, wherein the adhesive tab comprises:
- an intermediary body having a first side and an opposite second side;
- a first adhesive layer attached to the first side, the first adhesive layer comprising an acrylic adhesive covered by the liner; and
- a second adhesive layer attached to the second side, the second adhesive layer comprising a rubber adhesive secured to the device cover.

* * * * *